United States Patent
Jeon

(10) Patent No.: US 11,513,124 B2
(45) Date of Patent: *Nov. 29, 2022

(54) PROSTATE-SPECIFIC MEMBRANE ANTIGEN-BASED PROSTATE CANCER PATIENT SCREENING METHOD

(71) Applicant: CYTOGEN, INC., Seoul (KR)

(72) Inventor: Byung Hee Jeon, Seongnam-si (KR)

(73) Assignee: CYTOGEN, INC., Seoul (KR)

( * ) Notice: Subject to any disclaimer, the term of this patent is extended or adjusted under 35 U.S.C. 154(b) by 410 days.

This patent is subject to a terminal disclaimer.

(21) Appl. No.: 16/641,832

(22) PCT Filed: Jul. 17, 2018

(86) PCT No.: PCT/KR2018/008048
§ 371 (c)(1),
(2) Date: Feb. 25, 2020

(87) PCT Pub. No.: WO2019/050149
PCT Pub. Date: Mar. 14, 2019

(65) Prior Publication Data
US 2021/0164983 A1   Jun. 3, 2021

(30) Foreign Application Priority Data

Sep. 5, 2017   (KR) .................. 10-2017-0113298

(51) Int. Cl.
*G06T 7/00* (2017.01)
*G01N 33/574* (2006.01)
*G01N 21/64* (2006.01)

(52) U.S. Cl.
CPC ... *G01N 33/57434* (2013.01); *G01N 21/6428* (2013.01); *G01N 33/57492* (2013.01); *G06T 7/0012* (2013.01); *G01N 2021/6439* (2013.01); *G06T 2207/10024* (2013.01); *G06T 2207/10064* (2013.01); *G06T 2207/20036* (2013.01);

(Continued)

(58) Field of Classification Search
None
See application file for complete search history.

(56) References Cited

U.S. PATENT DOCUMENTS 9,739,783 B1    8/2017  Kumar et al.
2012/0148142 A1  6/2012  Ortyn et al.
(Continued)

FOREIGN PATENT DOCUMENTS

CN    102066547 A    5/2011
CN    103026228 A    4/2013
(Continued)

OTHER PUBLICATIONS

Werner, Shannon L., et al. "Analytical validation and capabilities of the epic CTC platform: enrichment-free circulating tumour cell detection and characterization." Journal of Circulating Biomarkers 4 (2015): 3. (Year: 2015).*

(Continued)

*Primary Examiner* — Sean M Conner
(74) *Attorney, Agent, or Firm* — Sughrue Mion, PLLC

(57) ABSTRACT

According to an embodiment of the present invention, there is provided a method of screening a prostate cancer patient by optical image analysis of a circulating tumor cell marker and a prostate-specific membrane antigen.

10 Claims, 10 Drawing Sheets

(52) U.S. Cl.
    CPC ............. *G06T 2207/20221* (2013.01); *G06T 2207/30024* (2013.01); *G06T 2207/30096* (2013.01)

(56) References Cited

U.S. PATENT DOCUMENTS

| | | | | |
|---|---|---|---|---|
| 2015/0233927 | A1* | 8/2015 | Giannakakou | G01N 21/6458 435/7.1 |
| 2016/0011198 | A1 | 1/2016 | Dittamore | |
| 2016/0340269 | A1* | 11/2016 | Muramatsu | C07C 1/2076 |
| 2020/0200757 | A1* | 6/2020 | Jeon | G01N 21/76 |
| 2020/0225238 | A1* | 7/2020 | Jeon | G01N 33/57434 |

FOREIGN PATENT DOCUMENTS

| | | |
|---|---|---|
| CN | 103642756 A | 3/2014 |
| CN | 103834558 A | 6/2014 |
| CN | 104073428 A | 10/2014 |
| CN | 104805011 A | 7/2015 |
| CN | 106076441 A | 11/2016 |
| CN | 107084916 A | 8/2017 |
| CN | 107262171 A | 10/2017 |
| KR | 10-1279918 B1 | 7/2013 |
| KR | 10-2017-0038724 A | 4/2017 |

OTHER PUBLICATIONS

Office Action dated Feb. 14, 2022 in Chinese Application No. 201880055755.8.

Min Wang, "Nutrition and culture media for animal cells", Bioengineering, China Medical Technology Press, 2015, pp. 113-115 (27 pages total).

Search Report dated Aug. 10, 2021 from China National Intellectual Property Administration in CN Application No. 201880055755.8.

Office Action dated Aug. 19, 2021 from China National Intellectual Property Administration in CN Application No. 201880055755.8.

Notice of Reasons for Refusal dated Mar. 2, 2021 from the Japanese Patent Office in JP Application No. 2020-512688.

Extended European Search Report dated Sep. 2, 2020 from the European Patent Office in Application No. 18854142.9.

"PSMA vs EpCAM Antibody Capture of Circulating Tumor Cells in Metastatic Castration-Resistant Prostate Cancer Patient", ABNOVA, Feb. 3, 2016, Retrieve from the Internet: URL:https://www.abnova.com/images/content/product/Application_Metastatic_CRPC_EpCAM_PSMA_CK.pdf.

Guiseppe Galletti et al., "Circulating Tumor Cells in Prostate Cancer Diagnosis and Monitoring: An Appraisal of Clinical Potential", Molecular Diagnosis and Therapy, vol. 18, No. 4, May 9, 2014, pp. 389-402 (22 pages total).

Se Young Choi et al., Circulating Tumor Cells Counts in Patients With Localized Prostate Cancer Including Those Under Active Surveillance, In Vivo: International Journal of Experimental and Clinical Pathophysiology and Drug Research, vol. 33, No. 5, Jan. 1, 2019, pp. 1615-1620 (6 pages).

Terence W. Friedlander et al., "Detection and Characterization of Invasive Circulating Tumor Cells Derived from Men with Metastatic Castration-Resistant Prostate Cancer", International Journal of Cancer, 2014, pp. 2284-2293, vol. 134.

International Search Report for PCT/KR2018/008048 dated Feb. 8, 2019 [PCT/ISA/210].

* cited by examiner

FIG. 7A
FIG. 7B
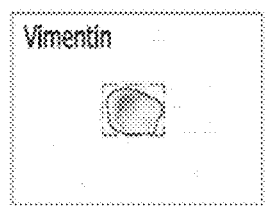
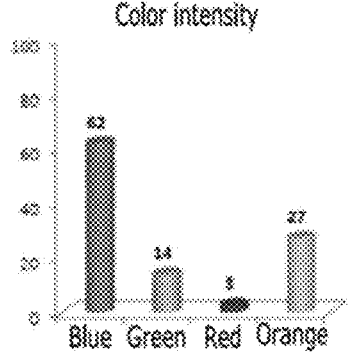
FIG. 7C
FIG. 7D
FIG. 7E

PROSTATE-SPECIFIC MEMBRANE ANTIGEN-BASED PROSTATE CANCER PATIENT SCREENING METHOD

CROSS REFERENCE TO RELATED APPLICATIONS

This application is a National Stage of International Application No. PCT/KR2018/008048 filed Jul. 17, 2018, claiming priority based on Korean Patent Application No. 10-2017-0113298 filed Sep. 5, 2017.

TECHNICAL FIELD

The present invention relates to a method for screening a prostate cancer patient, and more particularly to a method of screening a prostate cancer patient using circulating tumor cells by optical image analysis of prostate-specific membrane antigen and a marker of circulating tumor cells.

BACKGROUND ART

Prostate cancer is one of the most common cancers in men, and is the second most common cancer in the West, and the incidence of prostate cancer in South Korea has increased at the fastest rate among malignant tumors. Prostate cancer can be completely cured if it is confined to the prostate, and thus efforts have been made to detect prostate cancer early. Since prostate-specific antigen (PSA), a tumor marker for prostate cancer, was discovered in seminal fluid in 1971 and prostate tissue in 1979, it was initially introduced for post-treatment follow-up, but has been gradually used for a screening test. Serum prostate-specific antigen testing has been used extensively in clinical trials for screening since the late 1980s, has shown the best sensitivity among single test methods, and resulted in drastic changes in the diagnosis and treatment of prostate cancer. After the introduction of the prostate-specific antigen, the frequency of patients showing lymph node metastasis at the time of diagnosis was reduced to less than 5%, and the number of patients diagnosed as metastatic cancer at the time of initial diagnosis decreased drastically. Therefore, it has been estimated that the prostate-specific antigen exhibited the effect of early diagnosis of prostate cancer and stage migration to low stage disease. Despite this effect as a tumor marker, the biggest problems in using the prostate-specific antigen for a screening test are a lack of specificity and the possibility of overdiagnosis and overtreatment. Under this background, the necessity of developing a new tumor marker capable of replacing or supplementing the role of previous prostate-specific antigen has been raised, and in connection with this, prostate-specific membrane antigen (PSMA) has attracted attention as a new tumor marker. The prostate-specific membrane antigen is a membrane protein found in more than 90% of prostate cancers, but is also found in the blood vessels of most solid cancers. Therefore, targeting the prostate-specific membrane antigen can destroy prostate cancer itself and even the vascular structures that supply blood to the prostate cancer. Thus, the prostate specific membrane antigen has significant advantages.

In terms of treatment and prevention of prostate cancer, identifying patients who respond to or are likely to respond to prostate cancer treatments may be a goal for effective treatment of prostate cancer. Prostate cancer can be diagnosed using methods such as serum prostate-specific antigen testing, ultrasonography, tissue biopsy, and the like, and the expression pattern of prostate-specific membrane antigen can be examined by tissue biopsy. However, in the case of tissue biopsy, repetitive sampling from a patient is difficult and a physical burden can be imposed on the patient. Therefore, there is a need for a technology that can detect prostate-specific membrane antigen while reducing the burden on the patient.

DISCLOSURE

Technical Problem

An object of the present invention is to provide a method of screening a prostate cancer patient by detecting prostate specific membrane antigen, which is expressed in circulating tumor cells, by optical image analysis.

The technical objects to be achieved by the present invention are not limited to the above-mentioned object, and other technical problems which are not mentioned will be clearly understood by those skilled in the art from the following description.

Technical Solution

To achieve the above object, a method for screening a prostate cancer patient according to one aspect of the present invention may comprise the steps of:

obtaining blood from the prostate cancer patient;

isolating circulating tumor cells from the blood using a biochip;

reacting the isolated circulating tumor cells with a fluorescent marker binding specifically to the circulating tumor cells and a fluorescent marker binding specifically to prostate-specific membrane antigen;

receiving optical images of the circulating tumor cells reacted with the fluorescent marker specific to the circulating tumor cells and the prostate-specific membrane antigen reacted with the fluorescent marker specific to the prostate-specific membrane antigen under a plurality of wavelength ranges, respectively;

performing a first filtering by measuring fluorescence intensities of the circulating tumor cells and the prostate-specific membrane antigen in the optical images under all or part of the plurality of wavelength ranges;

performing a second filtering by measuring morphology of the circulating tumor cells in the optical images under all or part of the plurality of wavelength ranges; and performing a third filtering by measuring morphology of the circulating tumor cells in a combined image obtained by merging all or part of the optical images under the plurality of respective wavelength ranges.

In an embodiment of the present invention, the fluorescent marker which binds specifically to the circulating tumor cells may be at least one selected from the group consisting of an antibody specific for vimentin, an antibody specific for EpCAM, and an antibody specific for CK.

In an embodiment of the present invention, the optical images under the plurality of wavelength ranges in the step of receiving the optical images may include a blue wavelength range image, a green wavelength range image, and a red wavelength range image.

In an embodiment of the present invention, the nucleus of the circulating tumor cells may be identified by performing, on the blue wavelength range image, the step of performing the first filtering and the step of performing the second filtering.

In an embodiment of the present invention, the membrane of the circulating tumor cells may be identified by performing, on one or more of the green wavelength range image and the red wavelength range image, the step of performing the first filtering.

In an embodiment of the present invention, the morphology of the circulating tumor cells may include one or more of cell area, cell size, and circularity.

In an embodiment of the present invention, the step of performing the first filtering may comprise the steps of:

measuring the size of the circulating tumor cells in the optical images for all or part of the plurality of wavelength ranges; and setting a polygonal or circular area, which is larger than the measured size of the circulating tumor cells by a predetermined ratio or amount, and performing the first filtering by measuring the fluorescence intensity of the circulating tumor cells within the area.

In an embodiment of the present invention, the step of isolating the circulating tumor cells may be performed under a pressure of atmospheric pressure (1000 hPa) to 1020 hPa.

In an embodiment of the present invention, the biochip may be a high-density microporous chip coated with a BSA solution.

In an embodiment of the present invention, the high-density microporous chip may have size specificity.

In an embodiment of the present invention, coating with the BSA solution may be performed at a BSA concentration of 0.05 to 0.15%.

Advantageous Effects

According to an embodiment of the present invention, a prostate cancer patient may be screened by image analysis of prostate-specific membrane antigen (PSMA) which is expressed in circulating tumor cells.

It is to be understood that the effects of the present invention are not limited to the above-described effects and include all effects that can be deduced from the configuration of the present invention described in the detailed description of the invention or the claims.

DESCRIPTION OF DRAWINGS

FIGS. 7A-7E show the results of measuring the shapes and fluorescence intensities of circulating tumor cells bound with several fluorescent dyes or markers.

BEST MODE

Figure 1:
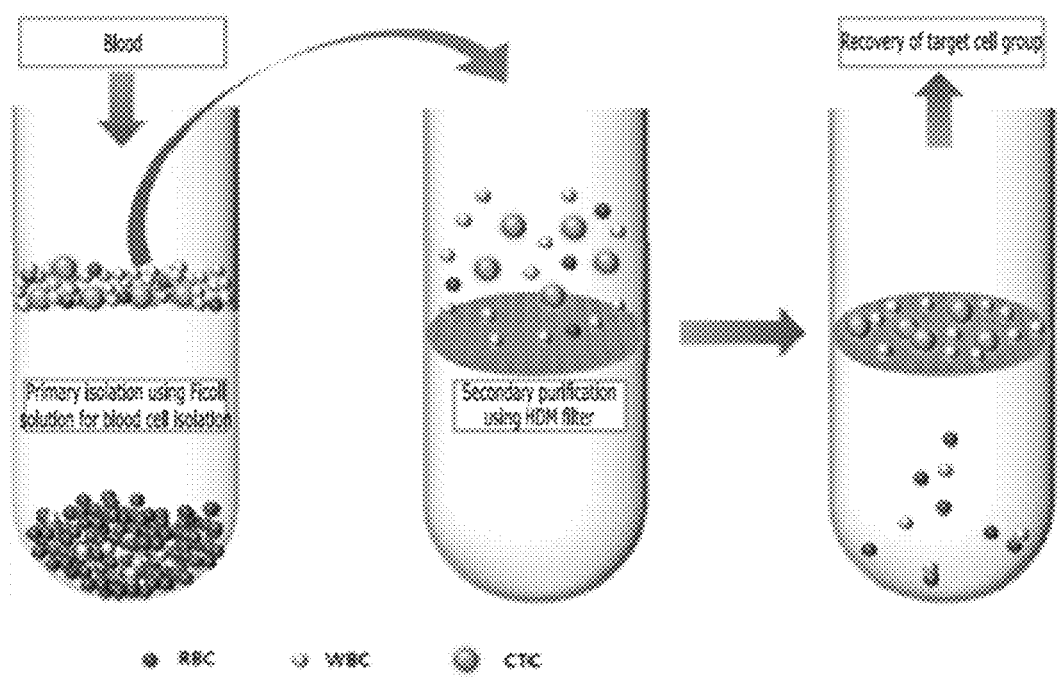
FIG. 1 shows a process of isolating circulating tumor cells.
Figure 2:
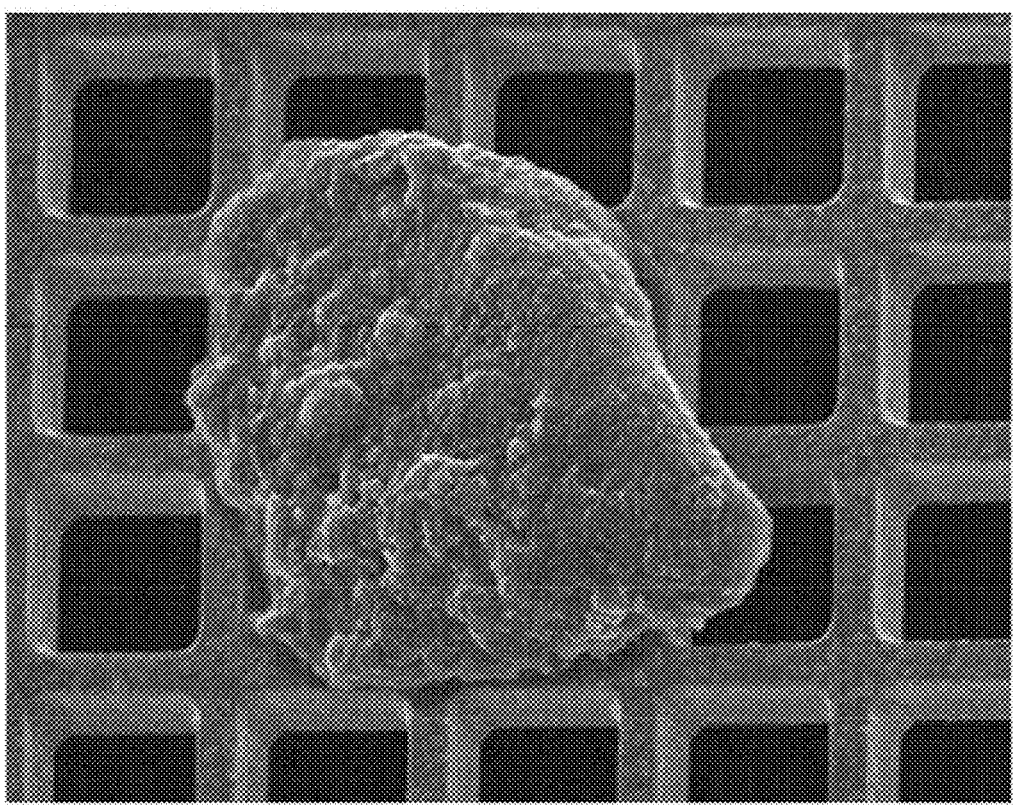
FIG. 2 is a photograph showing circulating tumor cells isolated by a high-density microporous chip.

Hereinafter, examples of the present invention will be described in detail so that those skilled in the technical field to which the present invention pertains can easily carry out the present invention. However, the present invention may be embodied in various different forms and is not limited to the examples described herein.

Example 1: Fabrication of High-Density Microporous Chip

A high-density microporous chip used in an experiment had a pore size of 5.5 to 8.5 µm and configured such that white blood cells (WBCs) and red blood cells (RBCs) having a size smaller than 5.5 µm would be removed by passage through the chip while target cells having a size larger than 5.5 µm would remain on the chip. Thus, it was a microporous chip designed such that it could selectively recover cells having a specific size.

For reference, an experiment was performed to examine the cell recovery rate of the high-density microporous chip. In the experiment, 10, 100 and 1000 cancer cells from cancer patients were spiked and passed through the chip, and the number of the cells on the chip (cell recovery rate) was examined. The results are shown in Table 1 below.

TABLE 1

| Samples | Number of cells spiked | Number of cells recovered | Cell recovery (%) |
|---|---|---|---|
| 1 | 10 | 9 | 90 |
| 2 | 100 | 86 | 86 |
| 3 | 1000 | 850 | 85 |

The results of calculating the cell recovery rate of the chip showed that the cell recovery rate was about 80% or higher. In order to confirm again that the recovered cells would be cancer cells, the cells were stained with CK antibody which has previously been used in a cancer assay. As a result, it was confirmed that the cells were all CK-positive, indicating that the cells were cancer cells.

Example 2: Process of Isolating Circulating Tumor Cells (CTCs)

1. Add 250 µl of an antibody polymer to 5 ml of blood, and then mix for about 3 seconds, followed by reaction at room temperature for 20 minutes.
2. Add 5 ml of PBS containing 1% FBS.
3. Carefully place 10 ml of the reaction solution in a 50 ml tube containing 15 ml of Ficoll solution.
4. Centrifuge the solution at 1200 g for 20 minutes to primarily remove blood cells.
5. To prevent the adsorption of unnecessary cells, coat a high-density (HD) microporous chip filter with 0.1% BSA solution for 10 minutes, followed by rinsing with PBS.
6. Place the supernatant of the Ficoll on the filter and filter out a trace amount of remaining red blood cells by gravity to secondarily isolate highly pure circulating tumor cells. Here, centrifugation or treatment such as immunobead treatment is not performed, thereby preventing the circulating tumor cells from being damaged.

7. Identify the isolated circulating tumor cells by staining.

Example 3: Short-Term Culture of Isolated Circulating Tumor Cells

The circulating tumor cells isolated by the high-density microporous chip according to the present invention were seeded onto an ultra-low attachment culture plate coated with a neutrally charged hydrophilic hydrogel. The culture plate contained a medium containing 11 ng/ml of insulin, 22 ng/ml of transferrin, 2 ng/ml of EGF and 8 µM of an ROCK inhibitor, and short-term culture of the cells was performed in a cell culture incubator at 37° C. under 5 to 10% CO2 for 14 days from the start of the culture.

Example 4: Confirmation of Circulating Tumor Cells

In order to confirm, by a staining method, that the circulating tumor cells subjected to short term culture according to Example 3 are cancer cells, a cell staining process was performed using the following method.

1. Perform a cytospin process which is a cytocentrifugation technique, and fix the collected cells to a slide for staining.
2. Perform a permeabilization process to enable antibody to enter the cells.
3. Perform a washing process with PBS.
4. Make 1% BSA (bovine serum albumin) using PBS and perform a blocking process to reduce non-specific binding and endogenous peroxidase activity.
5. Perform reaction with EpCAM (epithelial cell adhesion molecule), pan-CK (cytokeratin) and CD (cluster of differentiation) 45 as primary antibodies at room temperature for 60 minutes.
6. Perform reaction with fluorescently labeled secondary antibodies, which bind to the primary antibodies, at room temperature for 60 minutes.
7. Perform a washing process with PBS.
8. To finally stain the cell nucleus, add DAPI (4',6-diamidino-2-phenylindole) solution and cover the sample with a cover glass, followed by reaction at room temperature for 10 minutes.
9. Calculate the proportion of the stained cells and the cell recovery rate according to a manual while observing the stained cells.

Example 5: Fluorescence Image Analysis of Circulating Tumor Cells and Prostate-Specific Membrane Antigen 1. Prepare the circulating tumor cells which were fluorescently labeled in Example 4 above.
2. React the circulating tumor cells, which were fluorescently labeled in Example 4, with a primary antibody (mouse) specific for prostate-specific membrane antigen (rabbit mAb, cell signaling technology), followed by reaction with a secondary antibody (goat anti-rabbit IgG (H+L) cross-adsorbed secondary antibody, Alexa Fluor 546, Thermo), thereby fluorescently labeling the prostate-specific membrane antigen.
3. After the reaction, load the circulating tumor cells on a slide, and then place the slide on the platform of a Smart-Biopsy Cell Image Analyzer (CIA 020).
4. Image the cells in a plurality of set wavelength ranges, followed by measurement of the fluorescence intensity of the cells.
5. Perform a first filtering by measuring the fluorescence wavelengths of the circulating tumor cells and the prostate-specific membrane antigen in the fluorescence intensity measurement performed in the plurality of wavelength ranges.
6. Measure the fluorescence wavelengths (blue, green and red) of fluorescent markers (DAPI, EpCAM, CK and CD45) for the cell nucleus and membrane of the circulating tumor cells through the first filtering.
7. Perform a second filtering by measuring the cell area, cell size and circularity of the circulating tumor cells for the wavelengths of the fluorescent substances bound to the circulating tumor cells in the measured fluorescence wavelengths.
8. The second filtering includes a process of excluding CD45 (red)-stained cells while additionally measuring and analyzing the nucleus of the circulating tumor cells in the first filtered image.
9. Merge the first filtered image and the second filtered image together, and then perform a third filtering by measuring and analyzing the area, cell size and circularity of the circulating tumor cells.
10. Measure and digitize the intensity of each fluorescence wavelength.

Comparative Example 1: Medium-Dependent Change in Cell Count of Cultured Circulating Tumor Cells The division and growth of circulating tumor cells in a cell culture medium, which is generally used in cell culture, and in the culture medium according to the present invention, were comparatively tested. The culture medium that is generally used in cell culture contained 25 nM sodium selenite, 50 nM hydrocortisone, 0.01 mM ethanolamine, 0.01 mM phosphorylethanolamine, 100 pM triiodothyronine, 0.5% (w/v) bovine serum albumin, 10 mM HEPES, 0.5 mM sodium pyruvate, 4.5 mM L-glutamine and 1× antibiotic-antimycotic, and the culture medium according to the present invention was the same as that in Example 3. In addition, culture conditions were the same as those in Example 3, except that a normal culture plate was used.

Figure 3A:
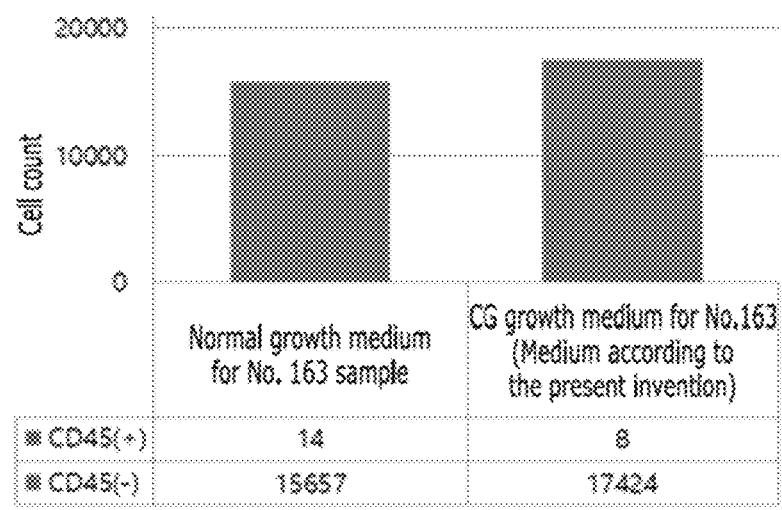
FIGS. 3A and 3B depict a graph showing the growth and division of circulating tumor cells cultured in a medium according to the present invention and the growth and division of circulating tumor cells cultured in a normal culture medium.
Figure 3B:
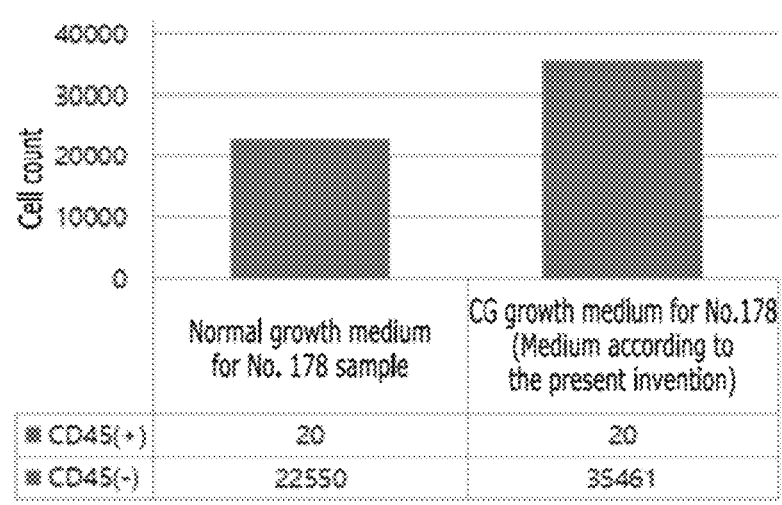
Figure 4A:
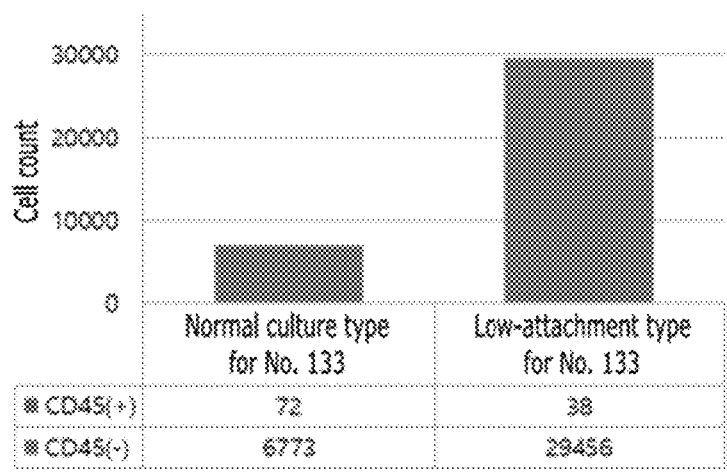
FIGS. 4A and 4B depict a graph showing the growth and division of circulating tumor cells cultured using a medium according to the present invention on a hydrogel-coated culture plate used in the present invention and the growth and division of circulating tumor cells cultured on a normal culture plate.
Figure 4B:
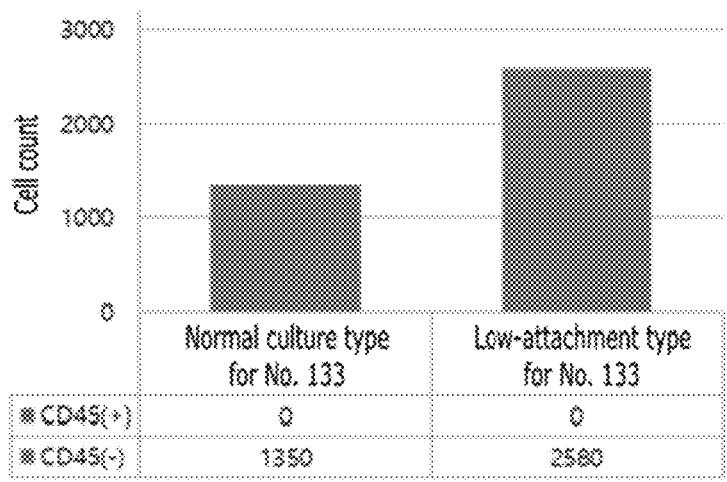

Referring to FIGS. 3A and 3B, CD45(-) is a biomarker for cells other than circulating tumor cells among the cultured cells, normal growth medium means a normal cell culture medium, and CG growth medium means the culture medium according to the present invention. FIGS. 3A and 3B show that the cell count of the circulating tumor cells cultured in the culture medium according to the present invention was higher. This suggests that the culture medium according to the present invention is more effective in the division and culture of circulating tumor cells than the normal culture medium.

The above description of the present invention is exemplary, and those of ordinary skill in the art to which the present invention pertains will appreciate that the present invention can be easily modified into other specific forms without departing from the technical spirit or essential characteristics of the present invention. Therefore, it should be understood that the exemplary embodiments described above are exemplary in all aspects and are not restrictive.

For example, each component described to be of a single type can be implemented in a distributed manner. Likewise, components described to be distributed can be implemented in a combined manner.

The scope of the present invention is defined by the claims described below. It shall be understood that all modifications and embodiments conceived from the meaning and scope of the claims and their equivalents are included in the scope of the present invention.

MODE FOR INVENTION

Hereinafter, the present invention will be described with reference to the accompanying drawings. However, the present invention may be embodied in various different forms, and thus is not limited to the embodiments described herein. In the drawings, parts irrelevant to the description are omitted for the simplicity of explanation, and like reference numerals designate like parts throughout the specification.

Throughout the specification, when any portion is referred to as being "connected, contacted or coupled" to another portion, this includes not only a case where any portion is "connected directly" to another portion but also a case where any portion is "connected indirectly" to another portion with one or more other elements interposed therebetween. In addition, it is understood that when any portion is referred to as comprising any component, it may further comprise one or more other components rather than excluding other components, unless otherwise specified.

Terms used in the present specification are only to describe specific embodiments and are not intended to limit the scope of the present invention. Singular expressions include plural expressions unless otherwise specified in the context thereof. In the present specification, it is to be understood that the terms "comprise", "have", etc., are intended to denote the existence of mentioned characteristics, numbers, steps, operations, components, parts, or combinations thereof, but do not exclude the probability of existence or addition of one or more other characteristics, numbers, steps, operations, components, parts, or combinations thereof.

Hereinafter, embodiments of the present invention will be described in detail with reference to the accompanying drawings.

A method for screening a prostate cancer patient according to one aspect of the present invention may comprise the steps of: (a) obtaining blood from the prostate cancer patient; (b) isolating circulating tumor cells from the blood using a biochip; (c) reacting the isolated circulating tumor cells with a fluorescent marker, which binds specifically to the circulating tumor cells, and a fluorescent marker which binds specifically to prostate-specific membrane antigen; (d) receiving optical images for a plurality of wavelength ranges, respectively, on the circulating tumor cells, which reacted with the fluorescent markers, and the prostate-specific membrane antigen; (e) performing a first filtering by measuring the fluorescence intensities of the circulating tumor cells and the prostate-specific membrane antigen in the optical images for all or part of the plurality of wavelength ranges; (f) performing a second filtering by measuring the morphology of the circulating tumor cells in the optical images for all or part of the plurality of wavelength ranges; and (g) performing a third filtering by measuring the morphology of the circulating tumor cells in a combined image obtained by merging all or part of the optical images under the plurality of respective wavelength ranges.

The circulating tumor cells (CTCs) mean tumor cells found in the peripheral blood of malignant tumor patients. The circulating tumor cells are very rare and the amount of samples available is very limited. Techniques for the detection and characterization of circulating cancer cells in blood include, but are not limited to, multiplex reverse transcriptase-quantitative polymerase chain reaction methods, imaging-based approaches, microfiltration techniques and microchip devices. The circulating tumor cells are liquid biopsy samples and can act as tumor biomarkers that can inevitably provide individualized treatment and post-treatment follow-up. In addition, the circulating tumor cells may be used as targets for understanding the biological characteristics of tumors and the seeding of tumor cells, but are not limited thereto. According to one embodiment of the present invention, the circulating tumor cells may be prostate cancer-derived cells.

The biochip is a hybrid device made in an existing semiconductor chip form by integrating and combining substances, such as organism-derived DNA, proteins, enzymes, antibodies, microorganisms, animal and plant cells and organs, and neurons, on a solid substrate made of an inorganic material such as a semiconductor. The biochip refers to a tool or device that uses the inherent functions of biomolecules to obtain biological information, such as gene expression patterns, gene binding or protein distributions, or speeds up biochemical processes and reactions or information processing.

The high-density microporous chip refers to a biochip capable of isolating a substance having a specific size based on the working principle of the biochip.

The high-density microporous chip is based on the size difference of blood cells and can capture circulating tumor cells with a recovery rate of about 90% within 10 minutes.

In an embodiment of the present invention, the pore size of the high-density microporous chip may preferably be 5.5 to 8.5 μm, more preferably 6.5 to 7.5 μm. If the pore size is smaller than 5.5 μm, red blood cells and white blood cells cannot be removed, because these cells remain on the chip without passing through the chip, and if the pore size is larger than 8.5 μm, circulating tumor cells cannot be selectively recovered, because the pore size is larger than the size of the circulating tumor cells and thus the circulating tumor cells pass through the chip. In one embodiment of the present invention, the pore shape of the high-density microporous chip may be circular, rectangular or elliptic, preferably rectangular.

In one embodiment of the present invention, the pores of the high-density microporous chip may be arranged in a regular pattern. In another embodiment of the present invention, the high-density microporous chip may be specifically made of stainless steel, nickel, aluminum, or copper. The pores may be formed by etching using MEMS (Microelectro Mechanical Systems) technology.

The spacing between two adjacent pores of the pores is narrower than the diameter of circulating tumor cells. According to one embodiment of the invention, the spacing between the two pores may be 45 to 65% relative to the diameter of circulating tumor cells. The high-density microporous chip is not deformed by the pressure of the blood or solution flowing through the channel.

After passing through the pores, the blood is discharged to the outside and the circulating tumor cells in the blood remain on the surface of the chip without passing through the pores. According to one embodiment of the present invention, the circulating tumor cells may be prostate cancer-derived cells.

Non-target cells, that is, red blood cells having a higher deformation rate than the circulating tumor cells, easily pass through the pores.

After filtration of the circulating tumor cells, the circulating tumor cells may be discharged to the outside by supplying a solution in the reverse or forward direction.

According to one embodiment of the present invention, the solution may be supplied in the reverse direction so as to minimize damage to the circulating tumor cancer cells. The solution may be supplied by a syringe, a syringe pump, a plunger pump, or the like. According to one embodiment of the present invention, the solution may be composed of a diluent, water and diluent acid, which dilute the blood. The circulating tumor cells discharged to the outside by supplying the solution may be easily collected in a container, for example, a test tube or a culture dish.

Meanwhile, circulating tumor cells having a diameter of 7.5 to 15 μm pass through a tube having a diameter of 8 μm when a pressure of about 100 mmHg is applied thereto. Circulating tumor cells having a diameter of 15 μm, which pass through the 8-μm diameter tube, have a deformation rate of about 53%. The spacing between two pores is preferably 4 μm or less in consideration of the deformation rate of the circulating tumor cells when the circulating tumor cells having a diameter of 7.5 μm are discharged to the outside by back washing, i.e., allowing the solution to flow in a direction opposite to the flow of the blood. Non-small cell lung cancer and breast cancer cells, for example, are known to have a diameter reaching about 40 μm. In consideration of the deformation rate of circulating cancer cells having a diameter of 40 μm during back washing, the spacing between two pores is preferably set to 21 μm or less. When circulating cancer cells having a diameter of 7.5 μm are present between two pores having a spacing larger than 4 μm, the circulating tumor cells may not be detached from the surface as they are deformed by the flow of the solution. In addition, tumor cells having a diameter of 40 μm may also not be detached from the surface between two pores having a spacing larger than 21 μm. In the high-density microporous chip according to the present invention, the spacing between two pores is 45 to 65% of the diameter of the circulating tumor cells in consideration of the pressure of the solution. If the spacing is larger than 65%, that is, larger than about 4.9 μm, circulating cancer cells having a diameter of 7.5 μm may not be detached from the surface between two pores by back washing. If the spacing is larger than 65%, that is, larger than 26 μm, circulating tumor cells having a diameter of 40 μm may not be detached from the surface between two pores by back washing. If the pressure of the solution is increased to forcibly detach the circulating tumor cells attached to the surface between two pores, damage to the circulating tumor cells may occur, which reduces the collection rate of living circulating tumor cells. If the spacing for circulating cancer cells having a diameter of 7.5 μm is less than 45%, that is, smaller than about 3.375 μm, the high-density microporous chip is highly likely to be damaged by the flow of the blood and the solution.

In one embodiment of the present invention, the sample may be repeatedly passed through the high-density microporous chip. Specifically, after circulating tumor cells are isolated once from the high-density microporous chip, the isolated circulating tumor cells may be loaded again on the high-density microporous chip and isolated, and the isolation process may be repeated.

In one embodiment of the present invention, isolation of the circulating tumor cells through the high-density microporous chip is not performed by applying a specific artificial pressure after loading the solution containing the circulating tumor cells onto the high-density microporous chip, but may be performed using gravity. Isolation of circulating tumor cells through the high-density microporous chip according to the present invention may minimize damage caused to the circulating tumor cells by artificial pressure, thereby maintaining the circulating tumor cells in the same state as when these cells are present in the body of the patient.

In one embodiment of the present invention, the high-density microporous chip may be coated with a specific material in order to minimize damage caused to the circulating tumor cells by the high-density microporous chip during isolation of the circulating tumor cancer cells, or to make the repeated use of the high-density microporous chip more efficient, or to make recovery of the circulating tumor cells more efficient. Specifically, the specific material may be an antibody that can bind specifically to the circulating tumor cells, and may also be any biomaterial that does not physically or chemically damage the cells. According to one embodiment of the present invention, the specific material may be BSA (bovine serum albumin) or an antibody. The antibody may be composed of, for example, an anti-epithelial cell adhesion molecule antibody (anti-EpCAM antibody), an anti-cytokeratin antibody (anti-CK antibody), or the like. According to a preferred embodiment of the present invention, the specific material may be BSA (bovine serum albumin).

The BSA (bovine serum albumin) solution refers to bovine serum albumin. It is a protein having a molecular weight of about 66.4 kDa, which is abundantly found in most animals. The BSA may be added as a nutrient to cells during cell culture in biochemistry/biology, and is also frequently used as a standard for obtaining a calibration curve in protein quantification. In addition, since a small amount of enzyme (protein) needs to be used when a restriction enzyme is used, the BSA may also be added to supplement the concentration of the protein in a solution. In addition, in various biochemical experiments (Western blotting, immunocytochemistry, ELISA, etc.), the BSA may also be used to prevent nonspecific binding, that is, prevent a specific antibody from binding to an unwanted protein or an unwanted position, before the specific antibody is attached to a protein to be detected.

According to one embodiment of the present invention, centrifugation may be used to allow peripheral blood to react with the high-density microporous chip coated with the BSA solution, thereby removing biopolymers other than the circulating tumor cells. According to one embodiment of the present invention, the isolation of the circulating tumor cells using the high-density microporous chip may be performed using gravity. Specifically, the isolation may be performed under a pressure of atmospheric pressure (1000 hPa) to 1020 hPa. Preferably, it may be performed under a pressure of atmospheric pressure (1000 hPa) to 1015 hPa. More preferably, it may be performed under a pressure of atmospheric pressure (1000 hPa) to 1013 hPa.

According to one embodiment of the present invention, the BSA solution may be coated on the upper surface or lower surface of the high-density microporous chip or the inner surface of the pores. Preferably, the BSA solution may be coated not only on the upper surface and lower surface of the high-density microporous chip, but also on the inner surface of the pores.

According to one embodiment of the present invention, coating with the BSA solution may be performed at a BSA concentration of 0.05 to 0.15%. According to a preferred embodiment of the present invention, coating with the BSA solution may be performed at a BSA concentration of 0.08 to 0.012%.

According to one embodiment of the present invention, coating with the BSA solution may be performed for 5 to 15 minutes. According to one preferred embodiment of the present invention, coating with the BSA solution may be performed for 8 to 12 minutes.

Referring to FIG. 1, in order to first remove blood cells from patient's blood, an antibody polymer is added to collected patient's blood and then mixed well, followed by reaction at room temperature. Thereafter, a PBS solution containing 1% FBS is added, Ficoll solution is placed on the reaction solution, and then the blood cells are primarily removed by centrifugation. After the blood cells which are unnecessary in the present invention are primarily removed as described above, red blood cells are filtered out using the high-density microporous chip specially coated with the BSA solution, thereby isolating highly pure circulating tumor cells. The isolated circulating tumor cells are identified by staining. When the high-density microporous chip coated with BSA is used, the circulating tumor cells to be isolated in the present invention may be isolated with minimal damage to the circulating tumor cells.

According to one embodiment of the present invention, after the step of isolating the circulating tumor cells from the blood by using the biochip, a step of performing short-term culture of the isolated circulating tumor cells may further be performed.

In one embodiment of the present invention, a culture medium that is used in the short-term culture may be composed of at least three selected from the group consisting of insulin, transferrin, EGF (epidermal growth factor) and an ROCK (Rho kinase) inhibitor.

The insulin is one of human metabolic hormones, is secreted from the Langerhans Island beta cells of the pancreas (organ) and serves to maintain the blood glucose level at a constant level. When the blood sugar level rises above a certain level, insulin is secreted and promotes the action of introducing blood glucose into cells and storing it again in the form of polysaccharide (glycogen). As the culture medium that is used in the short-term culture step according to the present invention contains insulin, it may further promote cell growth and division during culture of circulating tumor cells compared to a conventional culture medium for culturing circulating tumor cells. According to one embodiment of the present invention, the content of the insulin may be 3 to 50 ng/ml, 3 to 45 ng/ml, 3 to 40 ng/ml, 3 to 30 ng/ml, 4 to 50 ng/ml, 4 to 45 ng/ml, 4 to 30 ng/ml, 5 to 50 ng/ml, 5 to 45 ng/ml, or 5 to 30 ng/ml.

The transferrin, a kind of β-globulin, is an iron-transporting protein that binds to trivalent iron ions of two molecules absorbed in serum and supplies iron necessary for cell proliferation or hemoglobin production to cells through transferrin receptor. More than 99% of iron in serum binds to transferrin, and normally about one third of transferrin can bind to iron. As the culture medium that is used in the short-term culture step according to the present invention contains the transferrin, it can further promote cell growth and division during culture of circulating tumor cells compared to a conventional culture medium for culturing circulating tumor cells. According to one embodiment of the present invention, the content of the transferrin may be 3 to 50 ng/ml, 3 to 45 ng/ml, 3 to 40 ng/ml, 3 to 30 ng/ml, 4 to 50 ng/ml, 4 to 45 ng/ml, 4 to 30 ng/ml, 5 to 50 ng/ml, 5 to 45 ng/ml, or 5 to 30 ng/ml.

The epidermal growth factor (EGF) is a polypeptide growth factor that binds to epidermal growth factor receptor and promotes cell growth and division. In addition, the epidermal growth factor may induce ornithine decarboxylase in addition to promoting protein synthesis or RNA synthesis. As the culture medium that is used in the short-term culture step according to the present invention contains the epidermal growth factor, it may further promote cell growth and division during culture of circulating tumor cells compared to a conventional culture medium for culturing circulating tumor cells. According to an embodiment of the present invention, the content of the epidermal growth factor may be 0.5 to 10 ng/ml, 0.5 to 9 ng/ml, 0.5 to 8 ng/ml, 0.5 to 7 ng/ml, 0.5 to 6 ng/ml, 0.5 to 5 ng/ml, 0.7 to 10 ng/ml, 0.7 to 9 ng/ml, 0.7 to 8 ng/ml, 0.7 to 7 ng/ml, 0.7 to 6 ng/ml, 0.7 to 5 ng/ml, 1 to 10 ng/ml, 1 to 9 ng/ml, 1 to 8 ng/ml, 1 to 7 ng/ml, 1 to 6 ng/ml, or 1 to 5 ng/ml.

The Rho-associated protein kinase (ROCK) inhibitor refers to a compound capable of targeting Rho kinase (ROCK) and inhibiting or lowering the function of the Rho kinase. Here, the Rho kinase is a kinase belonging to the AGC family of serine-threonine kinases (PKA/PKG/PKC). The Rho kinase is involved in the process of controlling the movement and morphology of cells by acting on cytoskeleton. Specifically, the Rho kinase may act as a regulator of cell migration and actin organization. The Rho kinase is related to neurodegenerative diseases such as diabetes, hemorrhagic cerebrovascular disease, and Parkinson's disease, and the Rho kinase inhibitor can be used for the treatment and suppression of the Rho kinase-related diseases. According to one embodiment of the present invention, the ROCK inhibitor may be at least one selected from the group consisting of Fasudil, Ripasudil, RKI-1447 and Y27632. The Fasudil is one of ROCK inhibitors, and may be used for the treatment of cerebrovascular spasm and may also be effective in treating pulmonary hypertension. The Ripasudil, a derivative of the Fasudil, may act as a ROCK inhibitor and may also be used for the treatment of glaucoma or ocular hypertension. The RKI-1447 can suppress ROCK1 and ROCK2. The Y27632 can pass through cells and suppress ROCK1 and ROCK2 by competing with ATP for binding to the catalytic site of enzyme. According to one embodiment of the present invention, the ROCK inhibitor may be 3 to 30 µM, 3 to 27 µM, 3 to 24 µM, 3 to 21 µM, 4 to 20 µM, 4 to 30 µM, 4 to 27 µM, 4 to 24 µM, 4 to 21 µM, 4 to 20 µM, 5 to 30 µM, 5 to 27 µM, 5 to 24 µM, 5 to 21 µM, or 5 to 20 µM.

The culture plate that is used in the short-term culture according to the present invention may have a surface that prevents cell adhesion. According to one embodiment of the present invention, the circulating tumor cells may be cultured in a suspended state, and hence the surface of the culture plate may be coated to prevent cell adhesion. The surface of the culture plate may be coated with a hydrogel. The hydrogel refers to a gel containing water as a dispersion medium, and is formed when hydrosol loses its fluidity due to cooling or when a hydrophilic polymer having a three-dimensional network structure and a microcrystalline structure is swollen by water contained therein. Specifically, the hydrogel is a hydrophilic polymer crosslinked by interactions such as covalent bonds, hydrogen bonds, van der Waals bonds or physical bonds, and is a material having a three-dimensional polymer network structure capable of swelling in an aqueous solution by a large amount of water contained therein. In a state in which the hydrogel absorbed water as described above, the hydrogel shows a behavior similar to that of a living body tissue. The hydrogel may undergo a phase transition with a change in temperature, pH or the like, and hence the swelling rate thereof may discontinuously change. The hydrogel may be used for contact lenses, medical electrodes, and cell culture. According to one embodiment of the present invention, the hydrogel may be covalently coated on the culture plate and can prevent the circulating tumor cells from adhering to the surface of the culture plate. According to another embodiment of the present invention, the hydrogel may have hydrophilicity while having a neutral charge. The expression "having the neutral charge" means that the charge is neither positive nor negative, and the term "hydrophilicity" refers to a strong affinity for water, and means that the hydrogel can be easily dissolved in water.

In one embodiment of the present invention, the short-term culture step may be performed for 1 to 15 days from the start of the culture. In another embodiment of the present invention, it may be performed for 5 to 15 days, preferably 10 to 15 days. Even more preferably, it may be performed for 12 to 15 days.

The fluorescent marker that binds specifically to the circulating tumor cells refers to a fluorescent substance that may bind specifically to the circulating tumor cells themselves or to substances present inside or outside the circulating tumor cells. According to one embodiment of the present invention, the fluorescent marker capable of identifying the circulating tumor cells can bind specifically to the cell nucleus or bind specifically to the protein, DNA, RNA or the like present inside or outside the cells. Specifically, for binding to the cell nucleus, DAPI may be used as the fluorescent marker. Furthermore, a fluorescent marker that binds specifically to vimentin, an intermediate filament protein, may be used, and a fluorescent probe that binds specifically to prostate-specific antigen (PSA) may be used. In addition, a fluorescent marker that binds specifically to epithelial cell adhesion molecule (EpCAM) and cytokeratin (CK) may be used, and a fluorescent marker may also be used, which binds specifically to CD45 which is used as a means for removing non-target cells. The fluorescent marker that binds specifically to the circulating tumor cells may be composed of a nucleotide, an oligonucleotide, a peptide, a polypeptide, a nucleic acid or a protein, and may preferably be an antibody composed of protein. The fluorescent marker that binds specifically to the circulating tumor cells may be any substance that makes it possible to identify the circulating tumor cells by specific binding to the cells.

The prostate-specific antigen (PSA) is a proteolytic enzyme synthesized in epithelial cells of the prostate. It is rarely expressed in tissues other than the prostate, and thus is a useful biomarker which is used for screening prostate cancer. However, there are many limitations in screening prostate cancer patients using the prostate-specific antigen alone, and hence a biomarker may be used instead of, or in addition to, the prostate-specific antigen, and prostate-specific membrane antigen (PSMA) may be an example of this biomarker.

The prostate-specific membrane antigen (PSMA) is a kind of folate hydrolase secreted from the membrane of prostate epithelial cells, and is expressed in the central nervous system, normal small intestine and large intestine mucosa, renal tubules, or benign and malignant prostate epithelium tissue. It is most frequently produced in the prostate among these tissues. The prostate-specific membrane antigen may be expressed more in prostate cancer tissue than in normal prostate tissue, and the expression level thereof may be quantitatively measured by ELISA or Western blot assay. In addition, the prostate-specific membrane antigen may be used to determine the location of prostate cancer cells through an immunoscintigraphic test for diagnosing prostate cancer, after attaching an isotope to an antibody against the prostate-specific membrane antigen. The antibody against the prostate specific membrane antigen may be, for example, 7E11, an isotope of which may be indium 11.

The fluorescent marker that binds specifically to the prostate-specific membrane antigen may be a fluorescent substance that can bind specifically to the prostate-specific membrane antigen. Specifically, it may be an antibody that can bind specifically to the prostate-specific membrane antigen.

According to one embodiment of the present invention, prostate cancer patients may be identified or screened by image analysis of the prostate-specific membrane antigen and the circulating tumor cells. According to another embodiment of the present invention, image analysis of the prostate-specific membrane antigen and the circulating tumor cells makes it possible to predict the prognosis of prostate cancer patients or to perform the diagnosis and progress analysis of prostate cancer.

The optical images may be generated by an imaging system. According to one embodiment of the present invention, the imaging system may be a cell imaging system. The cell imaging system is a system configured to place stained cells on a platform such as a slide glass and observe and image the cells at various wavelengths. The cell imaging system may include an automated cell counting module, a fluorescence intensity analysis module, and a cytology-based cell classification/cognition module. In addition, as user convenience functions, a measurement function, a report automatic generation function and a DB management function may be included as user interfaces. This cell imaging system includes digital image analysis equipment for distinguishing cells, culture media, debris, and the like, and for identifying and counting desired cells by a user. The cell imaging system according to one embodiment of the present invention can accurately identify and count fluorescently labeled or marker-bound target cells from optical images.

The optical images may be optical images obtained by the light reflected from an object. The optical images of the cells may be output by the cell imaging system and may include images of cells, debris and the like on the background. Such optical images may be provided as a single image file made by stitching a plurality of divided images for the respective specific wavelength ranges. Here, the optical images under the plurality of wavelength ranges may include a blue wavelength range image, a green wavelength range image, and a red wavelength range image. The optical image for the blue wavelength range is particularly useful for the identification of the nucleus of the circulating tumor cells, and the optical images for the green and red wavelength ranges are particularly useful for the identification of the membrane of the circulating tumor cells. In addition, it is possible to identify specific fluorescent probes or markers by using the wavelength ranges of various colors.

In the first filtering or the second filtering, if the identification of the circulating tumor cells or the prostate-specific membrane antigen is not achieved at a desired level, it is possible to perform filtering of the optical image data and perform the first filtering or the second filtering once again, and it is also possible to perform the data filtering a plurality of times. In addition, after the first filtering or the second filtering is performed, the image data may be stored and output.

Furthermore, after performing the first filtering step and the second filtering step on the optical image for the first wavelength range, one or more of the first filtering step and the second filtering step on the optical image for the second wavelength range different from the first wavelength range may further be performed.

Figure 5A:
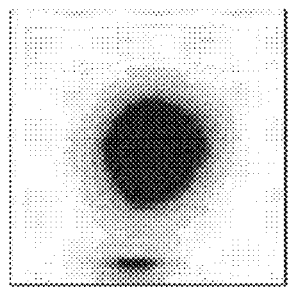
FIGS. 5A-5C depict a graph of optical images of circulating tumor cells for blue, green and red wavelength ranges.
Figure 5B:
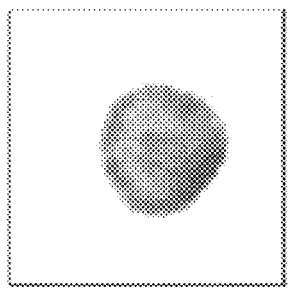
Figure 5C:
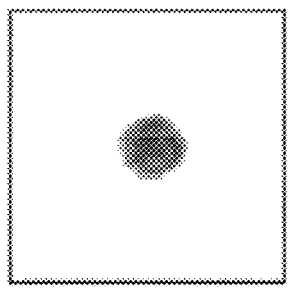

For example, the first wavelength range may be a blue wavelength range, and the second wavelength range may be a green or red wavelength range. In this case, the nucleus of the circulating tumor cells may be identified by performing the first filtering process and the second filtering process on the blue wavelength range image. In addition, the cell membrane of the circulating tumor cells may be identified by performing a first filtering process on one or more of the green wavelength range image and the red wavelength range image. These first and second filtering processes make it possible to accurately identify the cells from the optical image. For example, the green and red wavelength range images increase identification of target cells, for example, white blood cells and tumor cells. FIGS. 5A-5C show sample photographs of a blue wavelength range image FIG. 5A, a green wavelength range image FIG. 5B, and a red wavelength range image FIG. 5C for actual circulating tumor cells.

Meanwhile, in the second filtering process, the morphology of the circulating tumor cells is measured. Here, the morphology of the circulating tumor cells may include one or more of cell area, cell size (diameter), and cell circularity.

In one embodiment of the invention, measurement of the fluorescence intensity of the prostate-specific membrane antigen is performed by measuring the fluorescence intensity on the optical image of all or part of a plurality of wavelength ranges resulting from the fluorescence marker that binds specifically to the prostate-specific membrane antigen, and a first filtering thereon may be performed.

The process of performing the first filtering by measuring the fluorescence intensity of the circulating tumor cells other than the prostate-specific membrane antigen will now be described in more detail. The first filtering may be performed by measuring the cell size in an optical image of all or part of a plurality of wavelength ranges, and then setting a polygonal or circular area, which is larger than the measured cell size by a predetermined ratio or amount, and measuring the fluorescence intensity of the cells within this area.

FIGS. 7A-7E show the results of measurement of the morphology and fluorescence intensity of circulating tumor cells bound with various fluorescent dyes or markers. Specifically, FIGS. 7A-7E show a case where the nucleus of the cells was stained with DAPI FIG. 7A, a case where vimentin was used as a marker FIG. 7B, a case where an epithelial cell adhesion molecule (EpCAM) and cytokeratin (CK) were used as markers FIG. 7C, and a case where CD45 was used as a marker or a means for removing non-target cells FIG. 7D. In each of the cases, the first filtering may be performed by measuring the size of the cells in the optical image for the blue wavelength range, for example, and then setting a rectangle having a size which is at least 10% larger than the measured size, and measuring the fluorescence intensity of the cells within this rectangle. Subsequently, on optical images for the wavelength ranges of other colors, for example, green, red and yellow, fluorescence intensity measurement within areas having the same coordinates and sizes may be performed. FIGS. 7A-7D show images for blue, green, yellow and red wavelength ranges, respectively, and FIG. 7E shows the results of measuring the fluorescence intensity in each wavelength range image.

In the third filtering step, the third filtering is performed by measuring the morphology of the circulating tumor cells in a combined image obtained by merging all or part of the optical images under the plurality of wavelength ranges. Here, the morphology of the circulating tumor cells may include one or more of cell area, cell size, and cell circularity.

Figure 6:
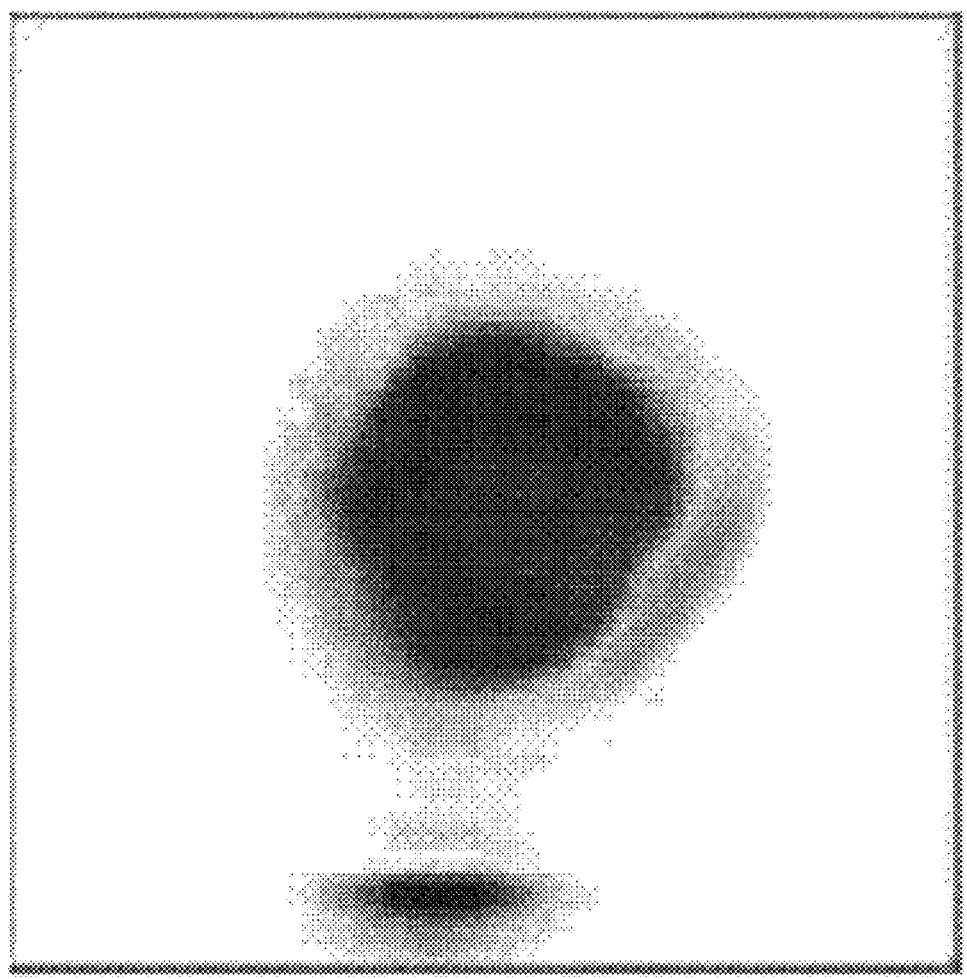
FIG. 6 is a photograph showing a combined image obtained by merging the optical images of circulating tumor cells shown in FIG. 5.

For example, as shown in FIG. 6, the third filtering may be performed by generating a combined image by merging the blue wavelength range image, the green wavelength range image and the red wavelength range image together, and measuring the morphology of the circulating tumor cells from the combined image.

The third filtering may be performed on the whole circulating tumor cancer cells, and may also be additionally performed on the cells which have been difficult to identify in the first and second filtering processes. If additional identification is required, separate data filtering may be performed or the third filtering may also be performed multiple times.

The image analysis may be executed by a computer program. This computer program may be implemented using one or more general-purpose or special-purpose computers, such as a processor, a controller, an arithmetic logic unit (ALU), a digital signal processor, a microcomputer, a field programmable gate array (FPGA), a programmable logic unit (PLU), a microprocessor, or any other devices capable of executing and responding to instructions.

Figure 8:
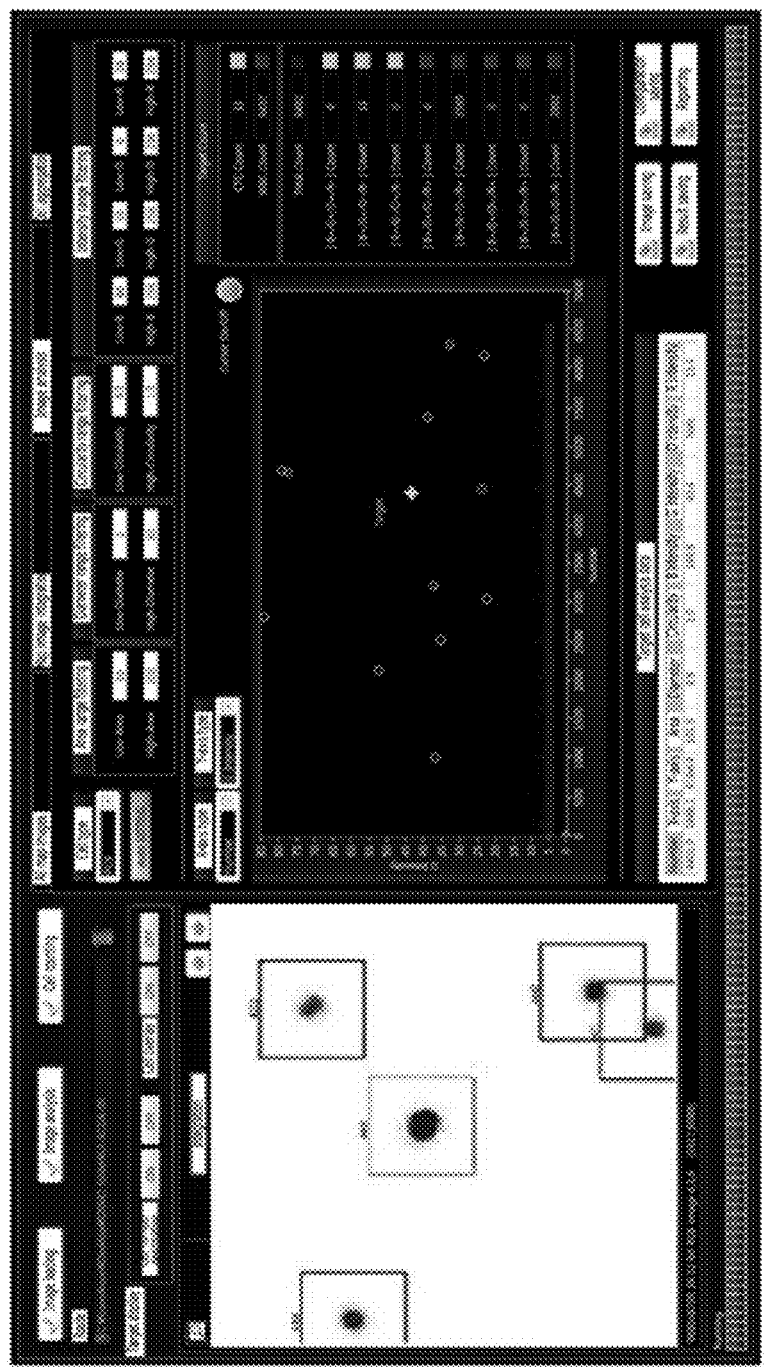
FIG. 8 shows a driving example of a program implementing an optical method for identifying circulating tumor cells.
Figure 9:
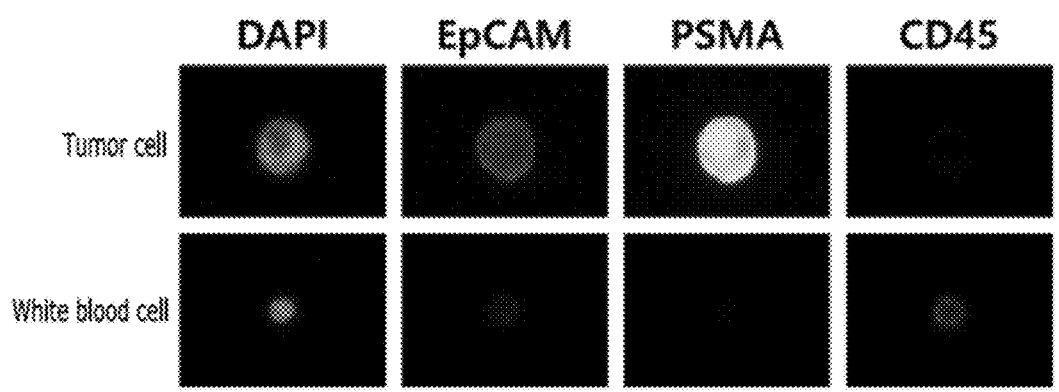
FIG. 9 shows DAPI, EpCAM, PSMA and CD45 immunofluorescence images of circulating tumor cells on slides spiked with prostate cancer cell line cells and white blood cells.
Figure 10A:
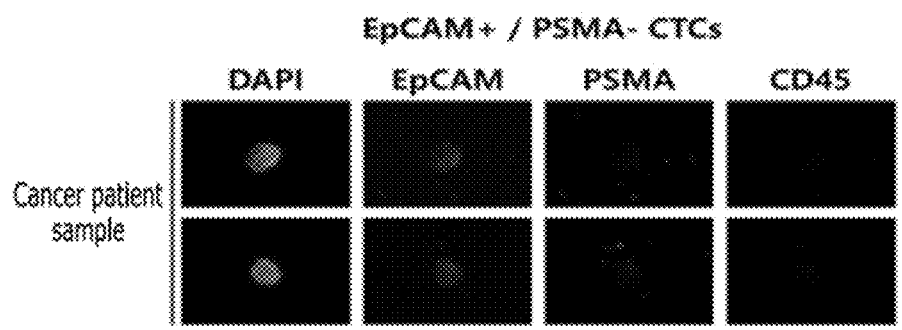
FIGS. 10A-10C show DAPI, EpCAM, PSMA and CD45 immunofluorescence images of circulating tumor cells in prostate cancer patient samples.
Figure 10B:
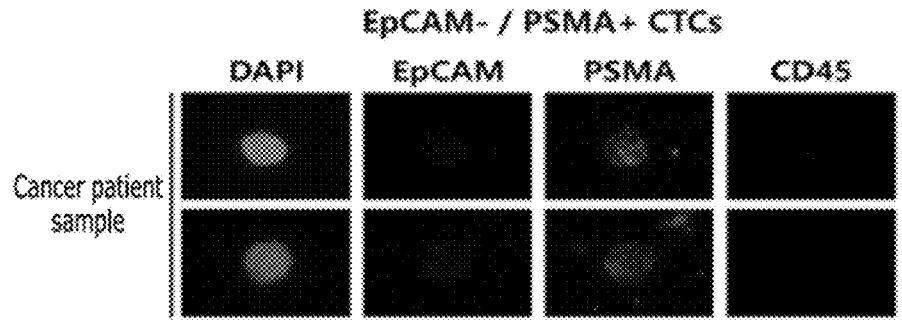
Figure 10C:
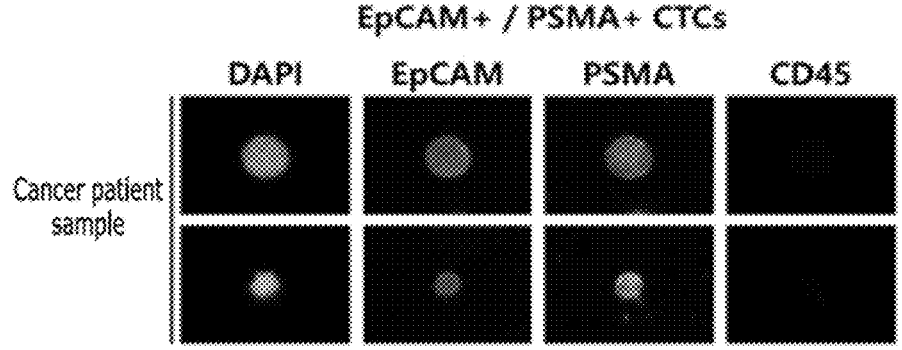

FIG. 8 shows a driving example of a program implementing image analysis, which is an example of a user interface of analysis software that implements the optical image analysis according to an embodiment of the present invention by an algorithm. With this software, cell identification and counting can be achieved automatically within a short time.

The invention claimed is:

1. A method for screening a prostate cancer patient, the method comprising the steps of:
   obtaining blood from the prostate cancer patient;
   isolating circulating tumor cells from the blood using a biochip;
   reacting the isolated circulating tumor cells with a fluorescent marker binding specifically to the circulating tumor cells and a fluorescent marker binding specifically to prostate-specific membrane antigen;
   receiving optical images of the circulating tumor cells reacted with the fluorescent marker specific to the circulating tumor cells and the prostate-specific membrane antigen reacted with the fluorescent marker specific to the prostate-specific membrane antigen under a plurality of wavelength ranges, respectively;
   performing a first filtering by measuring fluorescence intensities of the circulating tumor cells and the prostate-specific membrane antigen in the optical images under all or part of the plurality of wavelength ranges;
   performing a second filtering by measuring morphology of the circulating tumor cells in the optical images under all or part of the plurality of wavelength ranges; and
   performing a third filtering by measuring morphology of the circulating tumor cells in a combined image obtained by merging all or part of the optical images under the plurality of respective wavelength ranges, wherein the step of performing the first filtering comprises the steps of:
measuring a size of the circulating tumor cells in the optical images under all or part of the plurality of wavelength ranges; and
setting a polygonal or circular area, which is larger than the measured size of the circulating tumor cells by a predetermined ratio or amount, and performing the first filtering by measuring a fluorescence intensity of the circulating tumor cells within the area.

2. The method of claim 1, wherein the fluorescent marker binding specifically to the circulating tumor cells is at least one selected from the group consisting of an antibody specific for vimentin, an antibody specific for epithelial cell adhesion molecule (EpCAM), and an antibody specific for cytokeratin (CK).

3. The method of claim 1, wherein the optical images under the plurality of wavelength ranges in the step of receiving the optical images include a blue wavelength range image, a green wavelength range image, and a red wavelength range image.

4. The method of claim 3, wherein a nucleus of the circulating tumor cells is identified by performing, on the blue wavelength range image, the step of performing the first filtering and the step of performing the second filtering.

5. The method of claim 3, wherein a membrane of the circulating tumor cells is identified by performing, on one or more of the green wavelength range image and the red wavelength range image, the step of performing the first filtering.

6. The method of claim 1, wherein the morphology of the circulating tumor cells includes one or more of cell area, cell size, and circularity.

7. The method of claim 1, wherein the step of isolating the circulating tumor cells is performed under atmospheric pressure of 1000 hPa to 1020 hPa.

8. The method of claim 1, wherein the biochip is a high-density microporous chip coated with a bovine serum albumin (BSA) solution.

9. The method of claim 8, wherein the high-density microporous chip is a size-based chip.

10. The method of claim 8, wherein the coating with a BSA solution is performed at a BSA concentration of 0.05 to 0.15%.

* * * * *